(12) United States Patent
Nishijima et al.

(10) Patent No.: US 8,211,293 B2
(45) Date of Patent: Jul. 3, 2012

(54) METHOD OF CORRECTING $NO_x$ SENSOR AND $NO_x$-SENSING DEVICE

(75) Inventors: Hiroki Nishijima, Shizuoka-ken (JP);
Takeshi Hirabayashi, Toyota (JP);
Fumitaka Kato, Toyota (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 113 days.

(21) Appl. No.: 12/815,509

(22) Filed: Jun. 15, 2010

(65) Prior Publication Data
US 2010/0314264 A1  Dec. 16, 2010

(30) Foreign Application Priority Data
Jun. 16, 2009  (JP) ................................ 2009-143285

(51) Int. Cl.
*G01N 27/407* (2006.01)
(52) U.S. Cl. ........ 205/781; 205/785; 204/406; 204/424; 73/23.21; 73/23.31
(58) Field of Classification Search .................. 204/406, 204/424, 425; 205/781, 785; 73/23.21, 23.31; 702/24
See application file for complete search history.

(56) References Cited

U.S. PATENT DOCUMENTS

| | | | | |
|---|---|---|---|---|
| 7,294,252 | B2 * | 11/2007 | Wang et al. | 205/781 |
| 7,820,028 | B2 * | 10/2010 | Kroot et al. | 205/781 |
| 2003/0106808 | A1 * | 6/2003 | Miyata et al. | 205/761 |

FOREIGN PATENT DOCUMENTS

| | | |
|---|---|---|
| JP | 63-021548 | 1/1988 |
| JP | 02-001543 | 1/1990 |
| JP | 11-23526 | 1/1999 |
| JP | 11-023528 | 1/1999 |
| JP | 11-72477 | 3/1999 |
| JP | 2002-282942 | 10/2000 |
| JP | 2002-116180 | 4/2002 |
| JP | 2002-513934 | 5/2002 |
| JP | 2003-515166 | 4/2003 |
| JP | 2004-132841 | 4/2004 |
| WO | WO 99/57555 | 11/1999 |
| WO | WO 01/38864 | 3/2001 |

OTHER PUBLICATIONS

Office Action for German Appl. No. 10 2010 017 360.6 dated Mar. 1, 2012.

* cited by examiner

*Primary Examiner* — Kaj K Olsen
(74) *Attorney, Agent, or Firm* — Finnegan, Henderson, Farabow, Garrett & Dunner, LLP (57) ABSTRACT

A method of correcting $NO_x$ sensor includes the steps of preparing a corrective map in advance, finding an existing proportion of NO or $NO_2$ in a mixture of $NO_x$ in exhaust gases before coming into an $NO_x$ sensor, and correcting an $NO_x$ concentration that the $NO_x$ sensor detects actually. The corrective map records relationships between temperature physical quantities that are relevant to a temperature of the exhaust gases, oxygen-concentration physical quantities that are relevant to an oxygen concentration in the exhaust gases, and the existing proportion. The existing proportion is found with reference to the corrective map using the temperature physical quantities and oxygen-concentration physical quantities that are detected actually. The $NO_x$ concentration is corrected on the basis of not only the existing proportion but also a difference between an $NO_2$ diffusion velocity and an NO diffusion velocity.

12 Claims, 4 Drawing Sheets

METHOD OF CORRECTING $NO_x$ SENSOR AND $NO_x$-SENSING DEVICE

INCORPORATION BY REFERENCE

The present invention is based on Japanese Patent Application No. 2009-143,285, filed on Jun. 16, 2009, the entire contents of which are incorporated herein by reference.

BACKGROUND OF THE INVENTION

1. Field of the Invention

The present invention relates to technologies for detecting nitrogen oxides (hereinafter being abbreviated to as "$NO_x$") that exhaust gases include. More specifically, the present invention relates to a method of correcting $NO_x$ concentrations that $NO_x$ sensor detects actually. Moreover, the present invention relates to an $NO_x$-sensing device that comprises an $NO_x$ sensor, and a corrector for correcting $NO_x$ concentrations that the $NO_x$ sensor detects actually.

2. Description of the Related Art

An $NO_x$ sensor is a device for detecting $NO_x$ that exhaust gases include. For example, as Japanese Unexamined Patent Publication (KOKAI) Gazette No. 11-72,477 and Japanese Unexamined Patent Publication (KOKAI) Gazette No. 11-23,526 disclose, an $NO_x$ sensor has been usually disposed heretofore on an exhaust-gas flow passage's downstream side and/or upstream side with respect to an exhaust-gas converting catalyst that is put in place in the exhaust system of vehicle. Thus, the $NO_x$ sensor detects a concentration of $NO_x$ that exhaust gases include when the exhaust gases arrive at its vicinity.

Here, note however that the exhaust gases' $NO_x$ concentrations that the conventional $NO_x$ sensor detects differ slightly from the real or exact $NO_x$ concentrations in the exhaust gases. To be concrete, the exhaust gases' $NO_x$ concentrations that the conventional $NO_x$ sensor detects have been slightly lower than the real or exact $NO_x$ concentrations in the exhaust gases.

Moreover, the conventional $NO_x$ sensor, which is put in place on the exhaust-gas converting catalyst's upstream side and/or the downstream side, has been used for controlling the conversion actions of the catalyst and detecting the degradation. Accordingly, it is required for the $NO_x$ sensor to sense the $NO_x$ concentrations highly accurately. Consequently, it has been desired to devise a technology for making the $NO_x$ concentrations that the $NO_x$ sensor detects actually (hereinafter being referred to as "detected $NO_x$ concentrations or values") closer to the real or exact $NO_x$ concentrations (hereinafter being referred to as "true $NO_x$ concentrations or values"), or for approximating the true $NO_x$ concentrations or values by using the detected $NO_x$ concentrations or values.

SUMMARY OF THE INVENTION

The present invention has been developed in view of the aforementioned circumstances. It is therefore an object of the present invention to provide a method of correcting $NO_x$ sensor and an $NO_x$-sensing device, method and device which make it possible to make detected $NO_x$ concentrations or values closer to true $NO_x$ concentrations or values, or to make detected $NO_x$ concentrations or values equal to true $NO_x$ concentrations or values.

A method of correcting $NO_x$ sensor according to the present invention can achieve the aforementioned object. The present $NO_x$-sensor correcting method is adapted for correcting an $NO_x$ concentration that an $NO_x$ sensor detects actually, the $NO_x$ sensor being disposed in an exhaust-gas flow passage of vehicle, and comprising a porous diffusion-resistance layer, an exhaust-gas chamber into which exhaust gases that have passed through the porous diffusion-resistance layer are introduced, and a detective unit for detecting an $NO_x$ concentration in the exhaust gases that are introduced into the exhaust-gas chamber, and the $NO_x$-sensor correcting method comprises the steps of:

preparing a corrective map in advance, the corrective map recording relationships between temperature physical quantities that are relevant to a temperature of the exhaust gases, oxygen-concentration physical quantities that are relevant to an oxygen concentration in the exhaust gases, and an existing proportion of at least one of NO and $NO_2$ in a mixture of $NO_x$ in the exhaust gases before passing through the porous diffusion-resistance layer;

finding the existing proportion with reference to the corrective map using the temperature physical quantities that are detected actually and the oxygen-concentration physical quantities that are detected actually; and correcting the $NO_x$ concentration, which the $NO_x$ sensor detects actually, on the basis of not only the existing proportion but also a difference between an $NO_2$ diffusion velocity and an NO diffusion velocity.

Moreover, it is preferable to modify the method of correcting $NO_x$ sensor according to the present invention so that the detective unit can be provided with:

an oxygen-pumping electrode for discharging oxygen in the exhaust gases, which are introduced into the exhaust-gas chamber, to the outside of the exhaust-gas chamber;

an oxygen-detecting electrode for outputting an oxygen-detection electric current whose magnitude corresponds to a first amount of oxygen that remains inside the exhaust-gas chamber; and an $NO_x$-detecting electrode for outputting an $NO_x$-detection electric current whose magnitude corresponds to a sum of the first amount of oxygen and a second amount of oxygen that is contained in NO inside the exhaust-gas chamber;

the $NO_x$ sensor can detect an $NO_x$ concentration inside the exhaust-gas chamber on the basis of a difference between the oxygen-detection electric current and the $NO_x$-detection electric current; and the $NO_x$ concentration, which the $NO_x$ sensor detects actually, can be corrected by following expression (1):

$$\text{"}X\text{"} = \text{"}A\text{"}/(1+\text{"}B\text{"}\times\text{"}Z\text{"}-\text{"}Z\text{"}) \qquad (1)$$

wherein "X" specifies a corrected $NO_x$ concentration;

"A" specifies an $NO_x$ concentration that the $NO_x$ sensor detects actually;

"B" specifies a value that is obtained by dividing an $NO_2$ diffusion velocity by an NO diffusion velocity; and "Z" specifies a value that is obtained by dividing an $NO_2$ concentration in the exhaust gases before passing through the porous diffusion-resistance layer by a sum of the $NO_2$ concentration in the exhaust gases before passing through the porous diffusion-resistance layer and an NO concentration in the exhaust gases before passing through the porous diffusion-resistance layer.

An $NO_x$-sensing device according to the present invention can also achieve the aforementioned object, and comprises:

an $NO_x$ sensor being disposed in an exhaust-gas flow passage of vehicle, and comprising a porous diffusion-resistance layer, an exhaust-gas chamber into which exhaust gases that have passed through the porous diffusion-resistance layer are introduced, and a detective unit for detecting an $NO_x$ concentration in the exhaust gases that are introduced into the exhaust-gas chamber;

a corrective map recording relationships between temperature physical quantities that are relevant to a temperature of the exhaust gases, oxygen-concentration physical quantities that are relevant to an oxygen concentration in the exhaust gases, and an existing proportion of at least one of NO and $NO_2$ in a mixture of $NO_x$ in the exhaust gases before passing through the porous diffusion-resistance layer;

a first detector for detecting the temperature physical quantities;

a second detector for detecting the oxygen physical quantities; and a calculator for finding the existing proportion with reference to the corrective map using the temperature physical quantities that are detected actually and the oxygen-concentration physical quantities that are detected actually, and then correcting the $NO_x$ concentration, which the $NO_x$ sensor detects actually, on the basis of not only the existing proportion but also a difference between an $NO_2$ diffusion velocity and an NO diffusion velocity.

The $NO_x$-sensing device according to the present invention can preferably be modified to comprise the detector unit that can be provided with:

an oxygen-pumping electrode for discharging oxygen in the exhaust gases, which are introduced into the exhaust-gas chamber, to the outside of the exhaust-gas chamber;

an oxygen-detecting electrode for outputting an oxygen-detection electric current whose magnitude corresponds to a first amount of oxygen that remains inside the exhaust-gas chamber; and an $NO_x$-detecting electrode for outputting an $NO_x$-detection electric current whose magnitude corresponds to a sum of the first amount of oxygen and a second amount of oxygen that is contained in NO inside the exhaust-gas chamber;

the $NO_x$ sensor can detect an $NO_x$ concentration inside the exhaust-gas chamber on the basis of a difference between the oxygen-detection electric current and the $NO_x$-detection electric current; and the calculator can correct the $NO_x$ concentration, which the $NO_x$ sensor detects actually, by following expression (1):

$$\text{``}X\text{''}=\text{``}A\text{''}/(1+\text{``}B\text{''}\times\text{``}Z\text{''}-\text{``}Z\text{''}) \quad (1)$$

wherein "X" specifies a corrected $NO_x$ concentration;

"A" specifies an $NO_x$ concentration that the $NO_x$ sensor detects actually;

"B" specifies a value that is obtained by dividing an $NO_2$ diffusion velocity by an NO diffusion velocity; and "Z" specifies a value that is obtained by dividing an $NO_2$ concentration in the exhaust gases before passing through the porous diffusion-resistance layer by a sum of the $NO_2$ concentration in the exhaust gases before passing through the porous diffusion-resistance layer and an NO concentration in the exhaust gases before passing through the porous diffusion-resistance layer.

A conventional and usual $NO_x$ sensor is provided with a porous diffusion-resistance layer, an exhaust-gas chamber, and a detector unit. The detector unit detects a concentration of $NO_x$ (i.e., nitrogen oxides) inside the exhaust-gas chamber. Exhaust gases, which have passed through the porous diffusion-resistance layer, is introduced into the exhaust-gas chamber. The porous diffusion-resistance layer makes an exhaust-gas introduction passage that is directed from the outside of the exhaust-gas chamber to the inside, and plays a role of physically controlling the exhaust gases that are introduced into the exhaust-gas chamber so as to arrive at the detector unit eventually. Thus, the detector unit detects an $NO_x$ concentration in the exhaust gases that have passed through the porous diffusion-resistance layer.

As a result of the present inventor's dedicated studies, the present inventors found out the cause of the above-described inadequateness, that is, detected $NO_x$ concentrations or values that the conventional and usual $NO_x$ sensor detects have been lower than the true $NO_x$ concentrations or values. That is, the inadequateness results from the difference between an NO diffusion velocity and an $NO_2$ diffusion velocity.

Specifically, the exhaust gases pass or diffuse through the porous diffusion-resistance layer to reach the exhaust-gas chamber. Likewise, $NO_x$ being included in the exhaust gases also pass or diffuse through the porous diffusion-resistance layer to reach the exhaust-gas chamber.

Most of $NO_x$, which the exhaust gases include, are NO and $NO_2$. A diffusion velocity of $NO_2$ that passes through the porous diffusion-resistance layer is slower than a diffusion velocity of NO that passes through the porous diffusion-resistance layer, because the $NO_2$ molecules are bigger than the NO molecules. Accordingly, an $NO_2$ concentration of the exhaust gases, which have passed through the porous diffusion-resistance layer, that is, an $NO_2$ concentration of the exhaust gases inside the exhaust-gas chamber, is lower than another $NO_2$ concentration of the exhaust gases before passing through the porous diffusion-resistance layer, that is, an $NO_2$ concentration of the original or actual exhaust gases. Consequently, the resultant $NO_x$ detected concentration or value is lower than the true $NO_x$ concentration or value. In other words, the resultant $NO_x$ detected concentration or value is smaller than the true $NO_x$ concentration or value by the difference between the $NO_2$ concentration outside the exhaust-gas chamber and that inside the exhaust-gas chamber. Therefore, using the difference between the $NO_2$ diffusion velocity and the NO diffusion velocity makes it possible to find the difference between the $NO_2$ concentration outside the exhaust-gas chamber and that inside the exhaust-gas chamber. Then, the resulting difference enables exhaust-system engineers to carry out such a correction that makes the $NO_x$ detected concentration or value closer to the true $NO_x$ concentration or value, or that can approximate the $NO_x$ detected concentration or value to the true $NO_x$ concentration or value.

However, NO and $NO_2$ undergo reactions reversibly in the exhaust gases as shown in following equation (i), that is, NO react with oxygen to turn into $NO_2$, and $NO_2$ decomposes into NO and oxygen reversibly, or vice versa.

$$NO+(\tfrac{1}{2})\times O_2 \leftrightarrow NO_2 \quad (i)$$

Chemical equilibria shift depending on concentrations and temperatures. Therefore, the chemical equilibrium of the reaction according to above equation (i) shifts as well depending on temperatures of the exhaust gases and oxygen concentrations in the exhaust gases. To put it differently, existing proportions of NO in the exhaust gases, and existing proportions of $NO_2$ in the exhaust gases change in accordance with a temperature of the exhaust gases and an oxygen concentration in the exhaust gases. The temperature of the exhaust gases and the oxygen concentration in the exhaust gases can be detected readily, even though it is difficult to detect the existing proportions of NO and $NO_2$ in the exhaust gases with an $NO_x$ sensor. Therefore, it is possible to find the existing proportions of NO and $NO_2$ in the exhaust gases by means of setting the determination method as follows: namely; mapping the following data in advance: temperature physical quantities that are relevant to a temperature of the exhaust gases; oxygen-concentration physical quantities that are relevant to an oxygen concentration in the exhaust gases; and the existing proportions of NO and $NO_2$ in the exhaust gases before passing through an $NO_x$ sensor's porous diffusion-resistance layer (hereinafter being abbreviated to as the "existing proportions of NO and $NO_2$"); and then determining the existing proportions of NO and $NO_2$ by consulting the mapped data using the temperature physical quantities and oxygen-concentration physical quantities that are detected actually. Then, it is possible to find the difference between the $NO_2$ concentration outside the $NO_x$ sensor's exhaust-gas chamber and that inside the $NO_x$ sensor's exhaust-gas chamber highly reliably by correcting a detected $NO_x$ concentration or value, which the $NO_x$ sensor detects actually, on the basis of not only the thus found existing proportions of NO and $NO_2$ but also the above-described difference between the NO diffusion velocity and the $NO_2$ diffusion velocity. Thus, it is possible to make the detected $NO_x$ concentration or value much closer to the true $NO_x$ concentration or value, or to approximate the detected $NO_x$ concentration or value more accurately to the true $NO_x$ concentration or value.

As described above, in accordance with the $NO_x$-sensor correcting method and $NO_x$-sensing device according to the present invention, a detected $NO_x$ concentration or value in exhaust gases can be made virtually equal to the true $NO_x$ concentration or value therein by executing the following steps: finding an occurrence rate of NO or $NO_2$ in an $NO_x$ mixture in exhaust gases; finding a diffusion velocity of NO and another diffusion velocity of $NO_2$; and then correcting a detected $NO_x$ concentration or value that an $NO_x$ sensor senses actually based on the difference between the diffusion velocities of NO and $NO_2$ as well as on the occurrence rate of NO or $NO_2$, thereby approximating the detected $NO_x$ concentration or value of to the true $NO_x$ concentration or value.

Note that, in the present invention, the phrase, "temperature physical quantities that are relevant to temperatures of exhaust gases," can mean either actual temperatures of the exhaust gases, or can mean the other physical quantities. For example, it is allowable to indirectly calculate temperatures of exhaust gases or temperatures of catalysts based on temperatures of exhaust system's exhaust pipe to use the obtained data as the temperature physical quantities. Likewise, the phrase, "oxygen-concentration physical quantities that are relevant to oxygen concentrations of the exhaust gases," can mean either actual oxygen concentrations in the exhaust gases, or can mean the other physical quantities. That is, it is permissible to use air-fuel ratios, for instance, as the oxygen-concentration physical quantities.

In the meantime, it has been known generally that an $NO_x$ sensor is available which has an oxygen-pumping electrode, an oxygen-detecting electrode, and an $NO_x$-detecting electrode. The oxygen-pumping electrode discharges oxygen inside the $NO_x$ sensor's exhaust-gas chamber to the exhaust-gas chamber's outside. As a result, the chemical equilibrium in equation (i) above tilts or shifts to the left side in exhaust gases that are introduced into the exhaust-gas chamber and then go through the oxygen-pumping electrode. To put it differently, the oxygen-pumping electrode converts $NO_2$ in the exhaust gases, which are introduced into the exhaust-gas chamber, into NO.

Similarly to the oxygen-pumping electrode, the oxygen-detecting electrode discharges oxygen, which remains in the exhaust gases that have passed through the oxygen-pumping electrode, to the outside of the exhaust-gas chamber. Then, the oxygen-detecting electrode detects a concentration of oxygen, which remains in the exhaust gases, based on an electric current that occurs during the discharge (hereinafter being referred to as "oxygen detection current").

In the same manner as the oxygen-pumping electrode and oxygen-detection electrode do, the $NO_x$-detecting electrode discharges oxygen, which remains in the exhaust gases that have gone through the oxygen-detecting electrode, to the outside of the exhaust-gas chamber. Moreover, the $NO_x$-detecting electrode decomposes NO, which is present in the exhaust gases that are introduced into the exhaust-gas chamber, into nitrogen ions and oxygen ions, and then transports the oxygen ions to the outside of the exhaust-gas chamber. Thus, the $NO_x$-detecting electrode discharges oxygen, which the NO includes, to the outside of the exhaust-gas chamber. Then, based on an electric current that the discharge produces (hereinafter being referred to as "$NO_x$ detection current"), the $NO_x$-detecting electrode detects a concentration of $NO_x$ in the exhaust gases.

When using such an $NO_x$ sensor as the $NO_x$ sensor that is employed in the NOx-sensor correcting method and $NO_x$-sensing device according to the present invention, it is allowable to derive a computational expression for correcting an $NO_x$ concentration that the $NO_x$ sensor detects actually as described below, for instance. In the following formulas for calculations, "Z" designates a value that is obtained by dividing an $NO_2$ concentration in exhaust gases before passing through the $NO_x$ sensor's porous diffusion-resistance layer by a sum of the $NO_2$ concentration and an NO concentration in exhaust gases before passing through the porous diffusion-resistance layer. That is, "Z" corresponds to an existing proportion of $NO_2$ in the mixture of $NO_2$ and NO, i.e., an existing proportion which is directed to the present $NO_x$-sensor correcting method and $NO_x$-sensing device. Moreover, "B" is a value that is obtained by dividing an $NO_2$ diffusion velocity by an NO diffusion velocity. In other words, "B" is equivalent to the claimed "difference between an $NO_2$ diffusion velocity and an NO diffusion velocity." In addition, "A" designates a difference between an $NO_x$ detection current and an oxygen detection current.

Figure 1:
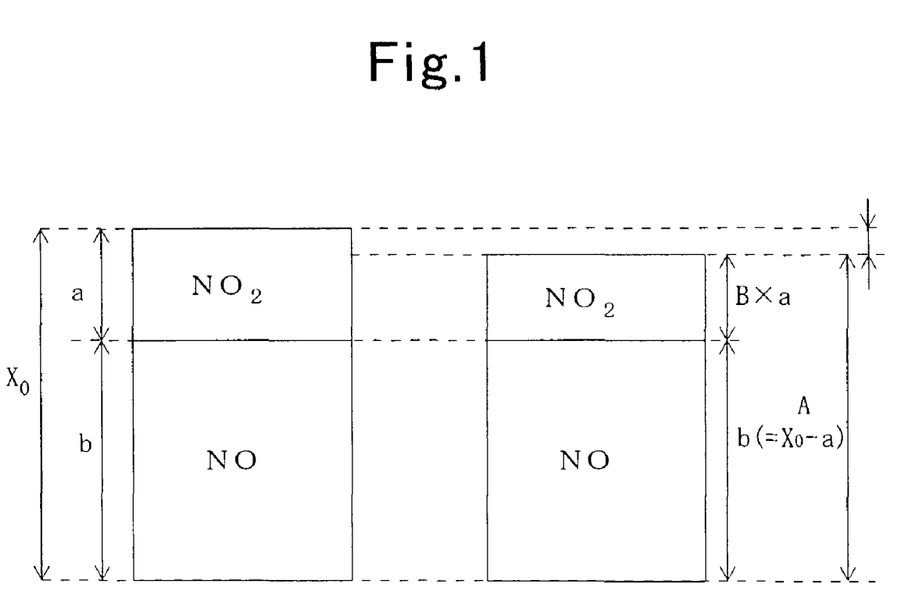
FIG. 1 is a diagram for schematically illustrating a relationship between a real or exact $NO_x$ value or concentration "$X_0$," an $NO_2$ concentration "a" in exhaust gases before passing through a porous diffusion-resistance layer, an NO concentration "b" in the exhaust gases before passing through the porous diffusion-resistance layer, and a detected $NO_x$ concentration or value "A."

As illustrated in FIG. 1, a real or exact $NO_x$ value or concentration "$X_0$" is a sum of the $NO_2$ concentration "a" and NO concentration "b" in exhaust gases that are prior to passing through the porous diffusion-resistance layer of the $NO_x$ sensor. On the other hand, a detective $NO_x$ value or concentration "A" that the $NO_x$ sensor detects is a sum of the following: the NO concentration "b"; and a product that is found by multiplying the $NO_2$ concentration "a" in exhaust gases that are prior to going through the porous diffusion-resistance layer by "B" (namely, the quotient that is found by dividing an $NO_2$ diffusion velocity by an NO diffusion velocity). In short, following equation (I) expresses the true $NO_x$ value or concentration "$X_0$," and another equation (II) below expresses the detected $NO_x$ value or concentration "A." Moreover, FIG. 1, equation (I) and equation (II) give still another equation (III) that expresses a relationship between the detected $NO_x$ value or concentration "A" and the true $NO_x$ value or concentration "$X_0$."

$$"X_0" = "a" + "b" \tag{I}$$

$$"A" = "b" + "B" \times "a" (\neq X_0) \tag{II}$$

$$\begin{aligned}"A" &= "B" \times "a" + "b" \\ &= "B" \times "a" + ("X_0" - "a") \\ &= "X_0" + "a" \times ("B" - 1)\end{aligned} \tag{III}$$

Moreover, an existing proportion of NO to $NO_x$ in exhaust gases before passing through the $NO_x$ sensor's porous diffusion-resistance layer equals to "Z," namely, the value that results from the division of the $NO_2$ concentration "a" in exhaust gases prior to going through the porous diffusion-resistance layer by a sum of the $NO_2$ concentration "a" and the NO concentration "b" in exhaust gases prior to going through the porous diffusion-resistance layer. Accordingly, following equation (IV) gives the $NO_2$ concentration "a" in exhaust gases prior to going through the porous diffusion-resistance layer.

$$\text{``}a\text{''} = \text{``}X_0\text{''} \times \text{``}Z\text{''} \quad \text{(IV)}$$

Consequently, it follows that equation (V) below, which expresses the true $NO_x$ value or concentration "$X_0$," derives from equations (III) and (IV) as shown below.

$$\begin{aligned}
\text{``}A\text{''} &= \text{``}X_0\text{''} + \text{``}a\text{''} \times (\text{``}B\text{''} - 1) \\
&= \text{``}X_0\text{''} + \text{``}X_0\text{''} \times \text{``}Z\text{''} \times (\text{``}B\text{''} - 1) \\
&= \text{``}X_0\text{''} \times (1 + \text{``}Z\text{''} \times \text{``}B\text{''} - \text{``}Z\text{''}) \\
\therefore \text{``}X_0\text{''} &= \text{``}A\text{''} / (1 + \text{``}Z\text{''} \times \text{``}B\text{''} - \text{``}Z\text{''})
\end{aligned} \quad \text{(V)}$$

A broad variety of values on "$X_0$," which were found by substituting a great variety of the detected $NO_x$ values or concentrations as well as the NO and $NO_2$ concentrations into "A," "B" and "Z" in above equation (V) were equal to the true $NO_x$ values virtually. Still, the resulting "$X_0$" values did not agree with the true $NO_x$ values completely. Therefore, the true $NO_x$ value or concentration "$X_0$" on the left side of equation (V) was replaced by "X," the corrected $NO_x$ concentration (or corrected $NO_x$ detection concentration or value), as established in above-described expression (1), that is, "X"="A"/(1+"Z"×"B"−"Z").

Note that it has been known that the $NO_2$ diffusion velocity is slower than the NO diffusion velocity by a factor of about 80%. Consequently, the term "B" in expression (1) or equation (V) above, namely, the value obtained by dividing the $NO_2$ diffusion velocity by the NO diffusion velocity, can be 0.8 approximately, or about 0.81 more accurately. In practical applications, however, it is allowable that the term "B" can fall in a range of from 0.79 to 0.82, or more preferably from 0.80 to 0.81.

BRIEF DESCRIPTION OF THE DRAWINGS

A more complete appreciation of the present invention and many of its advantages will be readily obtained as the same becomes better understood by reference to the following detailed description when considered in connection with the accompanying drawings and detailed specification, all of which forms a part of the disclosure.

DETAILED DESCRIPTION OF THE PREFERRED EMBODIMENTS

Having generally described the present invention, a further understanding can be obtained by reference to the specific preferred embodiments which are provided herein for the purpose of illustration only and not intended to limit the scope of the appended claims.

Other than the above-described $NO_x$ sensor that comprises an oxygen-pumping electrode, an oxygen-detecting electrode and an $NO_x$-detecting electrode, it is possible to use the other $NO_x$ sensors to make an $NO_x$ sensor, one of the constituent elements of the $NO_x$-sensor correcting method and $NO_x$-sensing device according to the present invention. For example, it is possible to make use of an $NO_x$ sensor that turns $NO_x$, which are involved in exhaust gases that flow through the porous diffusion-resistance layer and are then introduced into the exhaust-gas chamber, into a simple gas (e.g., NO). In such an $NO_x$ sensor, a catalyst, which facilitates the reaction, namely, $NO_2 \rightarrow NO$, is disposed on a more upstream side in the exhaust-gas flow passage than the porous diffusion-resistance layer and exhaust-gas chamber are disposed therein. In this instance as well, $NO_2$ is present slightly in the exhaust gases that go through the porous diffusion-resistance layer to reach the exhaust-gas chamber because of the reaction under chemical equilibrium as shown in above equation (i). Therefore, even when employing the other type of $NO_x$ sensor, it is possible to make a detected $NO_x$ concentration or value, which the $NO_x$ sensor detects actually, virtually equal to or approximate it to the true $NO_x$ concentration or value in the following manner as well: determining an existing proportion of NO or $NO_2$ in the mixture of $NO_x$ with reference to a corrective map, which is made up of temperature physical quantities and oxygen-concentration physical quantities that have been found out actually in advance; and then correcting the detected $NO_x$ concentration or value based on the resultant existing proportion of NO or $NO_2$ while taking the difference between an NO diffusion velocity and an $NO_2$ diffusion velocity into consideration.

In most applications, however, an $NO_x$ sensor that is directed to the $NO_x$-sensor correcting method and $NO_x$-sensing device according to the present invention usually comprises a porous diffusion-resistance layer, an exhaust-gas chamber, and a detective unit. The constituent elements will be hereinafter described in detail.

The porous diffusion-resistance layer serves as a layer for introducing exhaust gases into the inside of the exhaust-gas chamber with predetermined diffusion-rate controlling resistance. The porous diffusion-resistance layer can be made of a porous body that is made from alumina, for instance. Moreover, a nonporous body can be provided with pores to make the porous body.

An $NO_x$ sensor that is provided with paired oxygen-pumping electrodes, paired oxygen-detecting electrodes, and paired $NO_x$-detecting electrodes can be used to make the $NO_x$ sensor that is directed to the $NO_x$-sensor correcting method and $NO_x$-sensing device according to the present invention. In an $NO_x$ sensor like this, the paired oxygen-electrodes, paired oxygen-detecting electrodes and paired $NO_x$-detecting electrodes are disposed so as to interpose a solid electrolyte layer between them, respectively. When using this type of $NO_x$ sensor to make the $NO_x$ sensor being relevant to the present invention, it is possible to make the solid electrolyte layer from materials that exhibit oxygen-ion conductivity. As for the materials for making the solid electrolyte layer, the following can be used preferably: zirconium oxide (or zirconia), bismuth oxide, and cerium oxide (or ceria), for instance.

Moreover, it is allowable to further add yttrium oxide (or yttria), calcium oxide (or calcia), cerium oxide (or ceria) or magnesium oxide (or magnesia) to one of the major materials to use.

The oxygen-pumping electrodes and oxygen-detecting electrodes can preferably be made from a Pt—Au alloy. Pt—Au alloys can not only discharge oxide inside the exhaust-gas chamber to the outside of the exhaust-gas chamber but also they are less likely to interfere with the operations of the $NO_x$-detecting electrodes, the detection of $NO_x$, because they exhibit good oxygen sensitivity and show low selective reducibility to $NO_x$. Note that the "Pt—Au alloys" being set forth herein designate alloys whose major components are Pt and Au. However, it is allowable that the Pt—Au alloys can further comprise the other elements in trace amounts. Moreover, it is permissible that the oxygen-pumping electrodes and oxygen-detecting electrodes can be made from materials that differ from each another.

Moreover, the proportion of Pt to Au is not limited in particular in a Pt—Au alloy that makes the oxygen-pumping electrodes and oxygen-detecting electrodes. For reference, however, commonly-used oxygen-pumping electrodes and oxygen-detecting electrodes comprise Pt and Au in a Pt-to-Au ratio of from 99:1 to 90:10 by mass.

Meanwhile, it is preferable to use a Pt—Rh alloy as a material for making the $NO_x$-detecting electrodes, because Pt—Rh alloys can not only reduce $NO_x$ but also they are good in terms of oxygen sensitivity. Note that the "Pt—Rh alloys" being set forth herein involve alloys in which Pt and Rh make the major components, as well as alloys that are composed of, in addition to Pt and Rh, the other elements in trace amounts. Moreover, it is not limited especially in what a Pt-to-Rh proportion a Pt—Rh alloy, which makes the $NO_x$-detecting electrodes, comprises Pt and Rh. For reference, however, Pt and Rh make $NO_x$-detecting electrodes that have been used commonly in such a ratio of Pt to Rh that falls in a range of from 50:50 to 90:10 by mass.

EXAMPLE

Hereinafter, an example that is directed to the present invention will be described in detail. The example embodies the $NO_x$-sensor correcting method and $NO_x$-sensing device according to the present invention.

Figure 2:
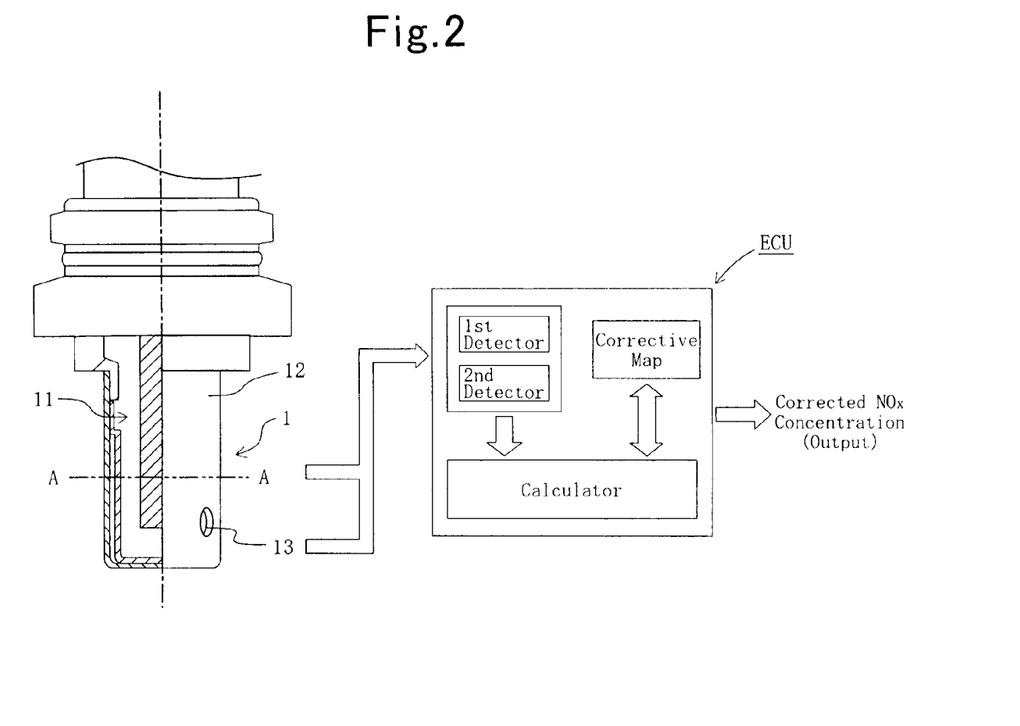
FIG. 2 is a front view that is cut off partially for schematically illustrating an $NO_x$ sensor that makes an $NO_x$-sensing device according to an example of the present invention.
Figure 3:
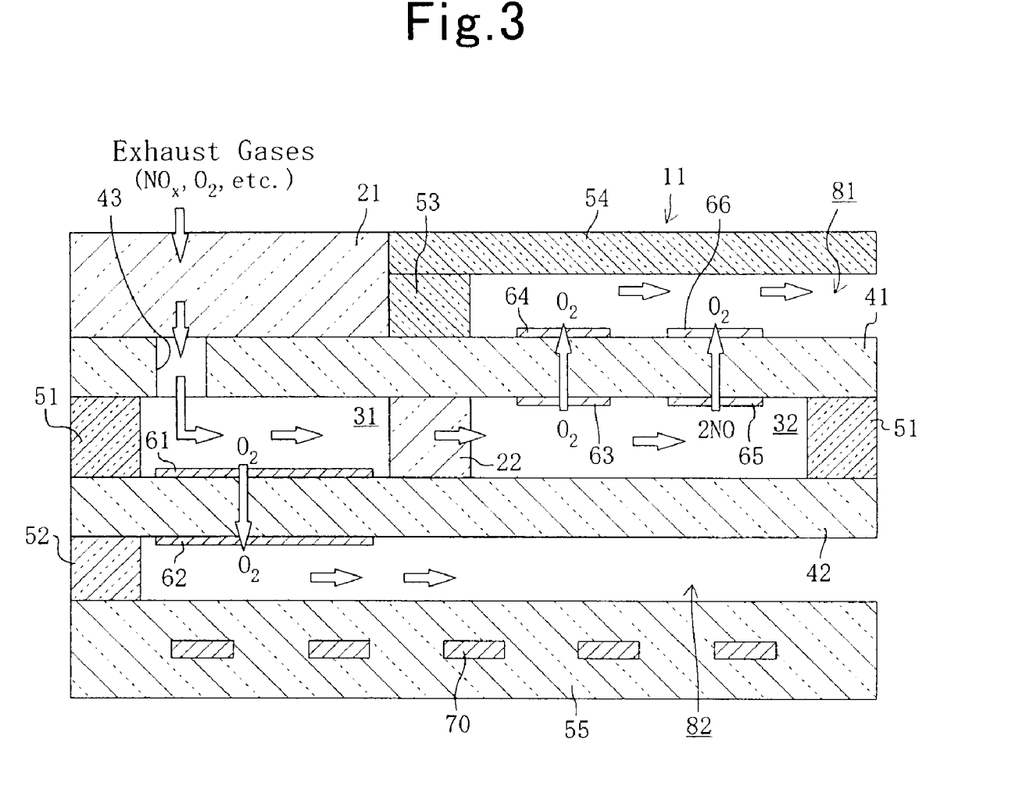
FIG. 3 is a cross-sectional view for schematically illustrating exhaust-gas chambers that make the $NO_x$-sensing device according to the present example, and constituent elements of a detective unit that makes the $NO_x$-sensing device.

An $NO_x$-sensing device that is directed to the example makes the $NO_x$-sensing device according to the present invention, and corrects a detected $NO_x$ concentration or value using the $NO_x$-sensor correcting method according to the present invention. A partially-cut-off front view, which schematically illustrates an $NO_x$ sensor that is directed to the $NO_x$-sensing device according to the example, is shown in FIG. 2. A cross-sectional view, which schematically illustrates exhaust-gas chambers and constituent elements of a detective unit that are directed to the $NO_x$-sensing device according to the example, is shown in FIG. 3.

$NO_x$-Sensing Device

The $NO_x$-sensing device according to the present example comprises an $NO_x$ sensor 1 (see FIGS. 2 and 3), a corrective map, a detector, and a calculator. In the present $NO_x$-sensing device, an engine control unit for vehicle (hereinafter abbreviated to as "ECU") is used to make the calculator. The ECU memorizes the corrective map. The detector is provided with a first detector for detecting temperature physical quantities, and a second detector for detecting oxygen-concentration physical quantities. For example, a thermometer comprising a thermo couple was used to make the first detector. The first detector can be disposed in an exhaust-gas flow passage of vehicle's exhaust system, and can detect the temperature of exhaust gases immediately before being introduced into the $NO_x$ sensor 1. Moreover, later-described paired oxygen pumping electrodes can be used to make the second detector.

As illustrated in FIG. 2, the $NO_x$ sensor 1 is made up of a sensing element 11, a casing 12, and the detector. Note that, in the present $NO_x$-sensing device, the ECU constitutes part of the detector as shown in the drawing.

The casing 12 is made of a metal, such as stainless steel or Inconel (trademark), and is formed as a cup shape substantially. A side wall of the casing 12 is provided with a casing-side exhaust-gas introduction port 13 that is formed as a through-hole shape. A bottom wall of the casing 12 is provided with a casing-side exhaust-gas discharge port (not shown) that is formed as a through-hole shape. The casing-side exhaust-gas introduction port 13 makes an inlet opening for introducing exhaust gases from the outside of the casing 12, namely, from the exhaust-gas flow passage, into the inside of the casing 12. The casing-side exhaust-gas discharge port makes an outlet opening for discharging exhaust gases from the inside of the casing 12 to the outside of the casing 12.

As shown in FIG. 3 explicitly, the sensor element 11 has a plurality of porous diffusion-resistance layers, a plurality of exhaust-gas chambers, and a detective unit. Note that two diffusion-resistance layers, a first diffusion-resistance layer 21 and a second diffusion-resistance layer 22, make the porous diffusion-resistance layers. Moreover, two chambers, a first chamber 31 and a second chamber 32, make the exhaust-gas chambers. The detective unit is made up of a plurality of solid electrolyte layers, a plurality of demarcator layers, a pair of oxygen-pumping electrodes, a pair of oxygen-detecting electrodes, a pair of $NO_x$-detecting electrodes, and a plurality of heaters 70. Note that two solid electrode layers, a first solid electrode layer 41 and a second solid electrode layer 42, make the solid electrolyte layers. Moreover, five demarcator layers, a first demarcator layer 51, a second demarcator layer 52, a third demarcator layer 53, a fourth demarcator layer 54 and a fifth demarcator layer 55, make the demarcator layers. In addition, two pumping electrodes, an inner pumping electrode 61 and an outer pumping electrode 62, make the paired oxygen-pumping electrodes. Moreover, two oxygen-detecting electrodes, an inner oxygen-detecting electrode 63 and an outer oxygen-detecting electrode 64, make the paired oxygen-detecting electrodes. In addition, two $NO_x$-detecting electrodes, an inner $NO_x$-detecting electrode 65 and an outer $NO_x$-detecting electrode 66, make the paired $NO_x$-detecting electrodes.

For example, the first diffusion-resistance layer 21 and second diffusion-resistance layer 22 are made of porous alumina, and allow exhaust gases to distribute through themselves. The first solid electrolyte layer 41 and second solid electrolyte layer 42 are made of a mixture of zirconia and yttria, and are formed as a substantially plate shape, respectively. The first, second, third, fourth and fifth demarcator layers 51, 52, 53, 54 and 55 are made of alumina. The inner pumping electrode 61 and inner oxygen-detecting electrode 63 are made of a Pt—Au alloy whose Pt-to-Au ratio is 99/1 (i.e., Pt:Au=99:1) by mass. The inner $NO_x$-detecting electrode 65 is made of a Pt—Rh alloy whose Pt-to-Rh ratio is 50/50 (i.e., Pt:Rh=50:50) by mass. The outer pumping electrode 62, outer oxygen-detecting electrode 64 and outer $NO_x$-detecting electrode 66 are made of Pt.

As illustrated in FIG. 3, the first solid electrolyte 41, and the second solid electrolyte 42 are disposed to face each other. The first solid electrolyte 41 is provided with a sensor-side exhaust-gas introduction port 43 that is formed as a through-hole shape. The sensor-side exhaust-gas introduction port 43 is covered with the first diffusion-resistance layer 21. The sensor-side introduction port 43 and first diffusion-resistance layer 21 make a passage for introducing exhaust gases into a later-described exhaust-gas chamber. The first demarcator layer 51 is formed as a frame shape, and is held as a thin layer between the first solid electrolyte layer 41 and the second solid electrolyte layer 42. The first diffusion-resistance layer 21, the first solid electrolyte layer 41, the second solid electrolyte layer 42, and the first demarcator layer 51 mark off or determine an exhaust-gas chamber. The second diffusion-resistance layer 22 divides the exhaust-gas chamber into two parts, namely, a first chamber 31 that involves or neighbors the sensor-side exhaust-gas introduction port 43 and a second chamber 32 that does not involve or neighbor the sensor-side exhaust-gas introduction port 43. The inner pumping electrode 61 is laminated, of the second solid electrolyte layer 42's faces, on one of the opposite faces that makes the first exhaust-gas chamber 31 (or the upward face in the drawing). The outer pumping electrode 62 is laminated, of the second solid electrolyte layer 42's faces, on the other one of the opposite faces that does not make the first exhaust-gas chamber 31, or that opposes the one of the opposite faces (or the downward face in the drawing). Moreover, of the first solid electrolyte layer 41's faces, the inner oxide-detecting electrode 63 and inner $NO_x$-detecting electrode 65 are laminated on one of the opposite faces that makes the second exhaust-gas chamber 32 (or the downward face in the drawing). Of the first solid electrolyte layer 41's faces, the outer oxide-detecting electrode 64 and outer $NO_x$-detecting electrode 66 are laminated on the other one of the opposite faces that does not make the second exhaust-gas chamber 32, or that opposes the one of the opposite faces (or the upward face in the drawing).

The inner and outer oxygen-detecting electrodes 63 and 64 are located at positions that are closer to the sensor-side exhaust-gas introduction port 43 than the inner and outer $NO_x$-detecting electrodes 65 and 66 are located. Moreover, the inner and outer oxygen-pumping electrodes 61 and 62 are located at positions that are much closer to the sensor-side exhaust-gas introduction port 43 than the inner and outer oxygen-detecting electrodes 63 and 64 as well as the inner and outer $NO_x$-detecting electrodes 65 and 66 are located. To put it differently, the inner and outer oxygen-pumping electrodes 61 and 62 are put in place on an upstream side of the exhaust-gas flow passage with respect to the inner and outer oxygen-detecting electrodes 63 and 64 as well as the inner and outer $NO_x$-detecting electrodes 65 and 66. Conversely, the inner and outer $NO_x$-detecting electrodes 65 and 66 are put in place on a downstream side of the exhaust-gas flow passage with respect to the inner and outer oxygen-pumping electrodes 61 and 62 as well as the inner and outer oxygen-detecting electrodes 63 and 64.

As shown in FIG. 3, the third demarcator layer 53 is laminated, of one of the first solid electrolyte layer 41's opposite faces, on the one of the opposite faces that is disposed oppositely to the second chamber 32 (or the upward face in the drawing). The third demarcator layer 53 is formed as a substantially letter-"U" shape, and adjoins the first diffusion-resistance layer 21. Moreover, of one of the third demarcator layer 53's opposite faces, the fourth demarcator layer 54 is laminated, on the one of the opposite faces that is disposed oppositely to the first solid electrode layer 41 (or the upward face in the drawing). The fourth demarcator layer 54 also adjoins the first diffusion-resistance layer 21. The first solid electrolyte layer 41, the third demarcator layer 53, and the fourth demarcator layer 54 mark off or determine a first exhaust-gas flow passage 81. The first exhaust-gas flow passage 81 is put in place in the vicinity of the casing-side exhaust-gas discharge port, and communicates with the outside of the casing 12, that is, the outside of the $NO_x$ sensor 1, by way of the casing-side exhaust-gas discharge port.

Likewise, of one of the second solid electrolyte layer 42's opposite faces, the second demarcator layer 52 is laminated on the one of the opposite faces that is disposed oppositely to the first chamber 31 (or the downward face), as illustrate in FIG. 3. The second demarcator layer 52 is formed as a substantially letter-"U" shape that opens in the same direction as the third demarcator layer 53 does. Moreover, of one of the second demarcator layer 52's opposite faces, the fifth demarcator layer 55, which is formed as a plate shape, is laminated on the one of the opposite faces that is disposed oppositely to the second solid electrolyte layer 42 (or the downward face in the drawing). The fifth demarcator layer 55 is provided with heaters 70 that are buried therein. The heaters 70 are connected with a not-shown outside electric power source to heat the sensor element 11. The second solid electrolyte layer 42, the second demarcator layer 52, and the fifth demarcator layer 55 mark off or determine a second exhaust-gas flow passage 82. The second exhaust-gas flow passage 82 is put in place in the vicinity of the casing-side exhaust-gas discharge port, and communicates with the outside of the casing 12 by way of the casing-side exhaust-gas discharge port.

Operations of $NO_x$ Sensor 1

Detailed descriptions will be made hereinafter on how the $NO_x$ sensor 1 that constitutes the $NO_x$-sensing device according to an example of the present invention operates while referring to the drawings.

Exhaust gases are introduced into the inside of the casing 12 through the casing-side exhaust-gas introduction port 13, and are then introduced into the first chamber 31 after passing through the first diffusion-resistance layer 21 and sensor-side exhaust-gas introduction port 43. The thus introduced exhaust gases first make contact with the inner oxygen-pumping electrode 61 that is exposed inside the first chamber 31. The inner oxygen-pumping electrode 61 ionizes oxygen, which is included in the exhaust gases that have contacted the inner oxygen-pumping electrode 61. Then, the ionized oxide goes through the second solid electrolyte layer 42, and eventually comes outside the first chamber 31 byway of the outer oxygen-pumping electrode 62 (that is, comes out of the first chamber 31 to the second exhaust-gas flow passage 82 through the outer oxygen-pumping electrode 62). On this occasion, the ECU, the claimed calculator that is connected with the inner and outer oxygen-pumping electrodes 61 and 62, reads out oxygen-pumping electric currents that the inner and outer oxygen-pumping electrodes 61 and 62 output, thereby calculating the oxide concentrations of the introduced exhaust gases. Moreover, the ECU calculates air-fuel ratios A/F based on the resulting oxygen concentrations. In addition, the ECU uses the thus calculated A/Fs as the claimed oxygen-concentration physical quantities in a later-described correction of $NO_x$ concentrations.

Meanwhile, $NO_x$, which the exhaust gases that are present inside the first chamber 31 include, are converted into or are reduced to NO, because the inner and outer oxygen-pumping electrodes 61 and 62 discharge oxygen, which the exhaust gases that are introduced into the first chamber 31 include therein, to the second exhaust-gas flow passage 82.

Moreover, the exhaust gases, which have contacted the inner oxygen-pumping electrode 61 but are present within the first chamber 31, then pass through the second diffusion-resistance layer 22, and come into the second chamber 32. The exhaust gases, which come into the second chamber 32, first make contact with the inner oxygen-detecting electrode 63. The inner oxygen-detecting electrode 63 ionizes oxygen, which remains in the exhaust gases that have contacted the inner oxygen-pumping electrode 61. Then, the ionized oxide passes through the first solid electrolyte layer 41, and eventually comes outside the second chamber 32 by way of the outer oxygen-detecting electrode 64 (that is, comes out of the second chamber 32 to the first exhaust-gas flow passage 81 through the outer oxygen-detecting electrode 64). On this occasion, the ECU, the claimed calculator that is connected with the inner and outer oxygen-detecting electrodes 63 and 64, reads out oxygen-detection electric currents that the inner and outer oxygen-detecting electrodes 63 and 64 output.

In addition, the exhaust gases, which have contacted the inner oxygen-detecting electrode 63 but are present within the second chamber 32, then make contact with the inner $NO_x$-detecting electrode 65. The inner $NO_x$-detecting electrode 65 decomposes NO, which is included in the exhaust gases that have contacted the inner $NO_x$-detecting electrode 65, into nitrogen ions and oxygen ions. Of the two ions, the oxide ions pass through the first solid electrolyte layer 41, and eventually come outside the second chamber 32 by way of the outer $NO_x$-detecting electrode 66 (that is, come out of the second chamber 32 to the first exhaust-gas flow passage 81 through the outer $NO_x$-detecting electrode 66). On this occasion, the ECU, the claimed calculator that is connected with the inner and outer $NO_x$-detecting electrodes 65 and 66, reads out $NO_x$-detection electric currents that the inner and outer $NO_x$-detecting electrodes 65 and 66 output. Moreover, the ECU calculates $NO_x$ concentrations (or detected $NO_x$ values) of the exhaust gases, which come into the second chamber 32, based on differences between the thus obtained oxygen-detection electric currents and $NO_x$-detection electric currents. The ionized oxygen, which has come out of the second chamber 32 to the first exhaust-gas flow passage 81, flows out to the surroundings by way of the not-shown casing-side exhaust-gas outlet or discharge port.

Corrective Map

Table 1 below gives a corrective map that the $NO_x$-sensing device according to this specific example of the present invention employs, for instance.

TABLE 1

|  | 15 ≦ A/F < 20 | 20 ≦ A/F < 30 | 30 ≦ A/F < 55 | 55 ≦ A/F < 60 |
| --- | --- | --- | --- | --- |
| 600 ≦ Temp. < 700 | 0.01036 | 0.06898 | 0.094846 | 0.11374 |
| 700 ≦ Temp. < 800 | 0.00457 | 0.03147 | 0.043937 | 0.05329 |
| 800 ≦ Temp. < 850 | 0.00234 | 0.01633 | 0.022940 | 0.02795 |
| 850 ≦ Temp. < 950 | 0.00175 | 0.01225 | 0.017243 | 0.02104 |

For example, the corrective map shown in Table 1 that is directed to the $NO_x$-sensing device according to the present example is made up of values on exhaust-gas temperatures, values on A/Fs, and values on existing proportions of $NO_2$ with respect to the mixture of NO and $NO_2$ before passing through the first porous diffusion-resistance layer 21 of the $NO_x$ sensor 1. As shown in Table 1, the corrective map records the relationships between the exhaust-gas temperatures, the A/Fs and the existing proportions of $NO_2$. Note that the exhaust-gas-temperature values serve as the claimed "temperature physical quantities," and the A/F values serve as the claimed "oxygen-concentration physical quantities." Moreover, values on existing proportions of NO with respect to the mixture of NO and $NO_2$ before passing through the first porous diffusion-resistance layer 21 can substitute for the values on the existing proportions of $NO_2$. The data that make the corrective map were collected by performing the following four steps, Steps #1 through #4.

Step #1

An NO-gas generator, a gas-mixing chamber, an electric heating furnace, an $NO_x$ sensor, a gas analyzer, and a thermometer were made ready. The $NO_x$ sensor was identical with the above-described $NO_x$ sensor according to the specific example of the present invention. The used gas analyzer was a chemiluminescent analyzer that was produced by HORIBA Co., Ltd. Note that the gas analyzer could detect NO concentrations and $NO_2$ concentrations individually or independently of each other. A thermocouple was used as the thermometer.

The employed NO-gas generator was composed of four gas bombs in which an oxygen gas, a propane gas, an NO gas and an $N_2$ gas were filled respectively. The NO-gas generator was connected with the gas-mixing chamber. The four gases were introduced into the gas-mixing chamber from the four gas bombs of the NO-gas generator, and were then mixed to produce mixture gases that contained exhaust-gas components like NO, $O_2$, HC and so on. Note that the feeding rates of the propane gas, NO gas and $N_2$ gas were set at a constant rate, respectively, during the introduction into the gas-mixing chamber. However, the feeding rate of the oxygen gas was changed gradually as described later while supplying it into the gas-mixing chamber.

The $NO_x$ sensor and thermometer were put in the gas-mixing chamber to expose them to the mixture gases inside the gas-mixing chamber. The gas-mixing chamber was connected with the gas analyzer by way of a ventilation pipe in order to flow the mixture gases within the gas-mixing chamber into the gas analyzer through the ventilation pipe. The gas-mixing chamber was put in the electric heating furnace, and was then heated with the electric heating furnace so that the mixture gases exhibited predetermined temperatures.

First of all, the temperature of the electric heating furnace was set so as to make the temperature of the mixture gases, which the thermometer detects, 600° C. Then, when the temperature of the mixture gases reached 600° C., the operation of the electric heating furnace was controlled so as to make the mixture gases keep exhibiting a constant temperature, 600° C.

Step #2

After the temperature of the mixture gases became constant, the feeding rate of the oxygen gas, which was fed from the NO-gas generator to the gas-mixing chamber, was adjusted so as to make the mixture gases inside the gas-mixing chamber exhibit an air-fuel ratio "A/F" of 15. Thereafter, the operation of the NO-gas generator was controlled so as to supply the oxygen gas, which NO-gas generator supplied to the gas-mixing chamber, in a gradually increasing feeding rate in order to make the air-fuel ratio "A/F" greater. In this instance, the NO concentrations and $NO_2$ concentrations in the mixture gases were detected by the gas analyzer every time the air-fuel ratio "A/F" rose by 1. Note that the air-fuel ratio "A/F" was calculated on the basis of the pumping electric currents that the inner and outer oxygen-pumping electrodes 61 and 62 of the $NO_x$ sensor 1 outputted. The gas analyzer kept on detecting the NO concentrations and $NO_2$ concentrations until the mixture gases within the gas-mixing chamber exhibited an air-fuel ratio "A/F" ratio of 60 approximately.

Step #3

After completing above-described Step #2, the operation of the electric heating furnace was controlled so as to raise the temperature of the mixture gases by 10° C. stepwise. Then, Step #2 was carried out repeatedly every time the temperature of the mixture gases rose by 10° C. Note that the repetitions of Step #2 were done until the mixture gases exhibited a temperature of 950° C. approximately.

Step #4

Finally, the corrective map shown in Table 1 above was prepared based on the data, such as the mixture-gas temperatures, the air-fuel ratios "A/F," the NO concentrations and the $NO_2$ concentrations, that Step #2 and Step #3 yielded. Concretely speaking, an existing proportion of $NO_2$ (i.e., "Z"), namely, a quotient being found by dividing the $NO_2$ concentration by a sum of the NO concentration and $NO_2$ concentration, was calculated for every temperature and air-fuel ratio "A/F" of the mixture gases. Moreover, the temperatures and air-fuel ratios "A/F" of the mixture gases were divided into a predetermined range, respectively. Then, an average value of the thus found $NO_2$'s existing proportions "Z," which fell in each of the divided ranges, was calculated. For example, in the corrective map given in Table 1, the temperatures of the mixture gases were divided into the following four specific ranges: from 600° C. or more to less than 700° C. (more precisely, from 600° C. to 690° C.); from 700° C. or more to less than 800° C. (more precisely, from 700° C. to 790° C.); from 800° C. or more to less than 850° C. (more precisely, from 800° C. to 840° C.); and from 850° C. or more to less than 950° C. (more precisely, from 850° C. to 940° C.). Likewise, the air-fuel ratios "A/F" of the mixture gases were divided into the following four specific ranges: from 15 or more to less than 20 (more precisely, from 15 to 19); from 20 or more to less than 30 (more precisely, from 20 to 29); from 30 or more to less than 55 (more precisely, from 30 to 54); and from 55 or more to less than 60 (more precisely, from 55 to 59). Thus, the corrective map that is directed to the $NO_x$-sensing device according to the present example was formulated by conducting Steps #1 through #4 as described above.

Correcting $NO_x$ Concentrations

The ECU, the claimed calculator, that is directed to the $NO_x$-sensor correcting method and $NO_x$-sensing device according to the present invention, corrects $NO_x$ concentrations (or detected $NO_x$ values), which the $NO_x$ sensor 1 detects, using the existing proportions of $NO_2$ with respect the mixture of NO and $NO_2$ and the difference between an NO diffusion velocity and an $NO_2$ diffusion velocity.

More specifically, the ECU uses a numeric value, 0.81, as the difference between an NO diffusion velocity and an $NO_2$ diffusion velocity. Note that the numeric value, 0.81, is the term "B" of aforementioned expression (1), "X"="A"/(1+ "B"×"Z"–"Z"), that results from dividing an $NO_2$ diffusion velocity by an NO diffusion velocity. Moreover, the ECU uses existing proportions of $NO_2$ with respect the mixture of NO and $NO_2$ as numeric values "Z." The numeric values "Z" are findable by referring to the corrective map shown in Table 1 using exhaust-gas temperatures and air-fuel ratios "A/F" that the above-described $NO_x$-sensing device according to the present example detects. As aforementioned, the exhaust-gas temperatures make the claimed temperature physical quantities, and the air-fuel ratios "A/F" make the claimed oxygen-concentration physical quantities. Then, the ECU corrects the $NO_x$ concentrations (or detected $NO_x$ values), which the $NO_x$ sensor 1 detects actually, by substituting the thus obtained "B," "Z" and $NO_x$ concentrations (or detected $NO_x$ values) "A" into the respective terms in expression (1) above. Thus, the ECU calculates the corrected values "X," namely, the corrected $NO_x$ concentrations (or corrected $NO_x$ detection values).

Evaluation Test

The $NO_x$-sensing device according to the present example was evaluated on how precisely it detected $NO_x$ concentrations by comparing the following:

the corrected values "X" for $NO_x$ concentrations (or corrected $NO_x$ concentrations or values), corrected values "X" which the $NO_x$-sensing device according to the present example calculated;

the $NO_x$ concentrations (or detected $NO_x$ concentrations or values) that the $NO_x$ sensor 1, which was relevant to the $NO_x$-sensing device according to the present example, detected actually; and the real or exact $NO_x$ concentrations (or true $NO_x$ values) in the exhaust gases that were fed into the $NO_x$-sensing device according to the present example.

Figure 4:
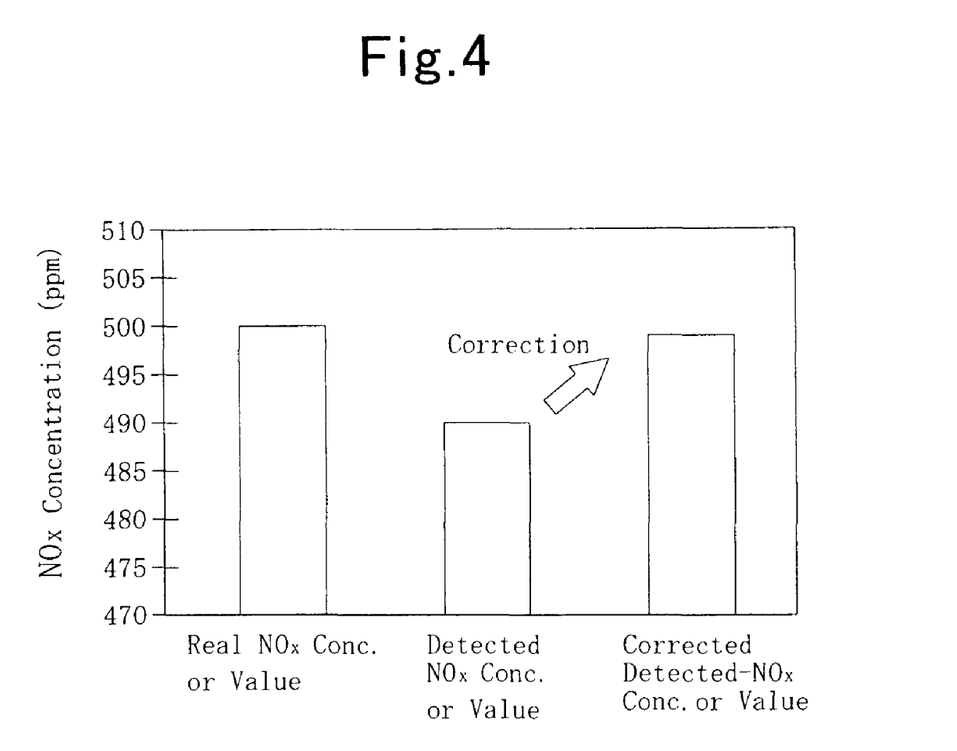
FIG. 4 is a bar chart for illustrating the result of a test for evaluating the $NO_x$-sensing device according to the present example.

Concretely speaking, model gases were prepared. Note that the prepared model gases had compositions that were analogous to or simulated those of the exhaust gases. The $NO_x$ concentrations of the model gases were detected with the gas analyzer that was used in collecting data for making the above-described corrective map that is relevant to the $NO_x$-sensing device according to the present invention. Moreover, the $NO_x$ concentrations, A/Fs and temperatures of the model gases were detected using the $NO_x$-sensing device according to the present example. Then, the real or exact $NO_x$ concentrations (or true $NO_x$ concentrations or values) of the model gases that the gas analyzer detected were compared with $NO_x$ concentrations (or detected $NO_x$ concentrations or values) that were prior to the correction by the ECU, the claimed calculator, (or that had not underwent the correction), and with the corrected values "X," that is, $NO_x$ concentrations (or corrected detected-$NO_x$ concentrations or values) that were after the correction (or that had underwent the correction). FIG. 4 illustrates one of the results of the evaluation test in a bar chart.

As shown in FIG. 4, the gas analyzer exhibited an $NO_x$ concentration (or actual $NO_x$ concentration or value) of 500 ppm for a model gas in the evaluation test, for instance. The $NO_x$-sensing device according to the present example showed that the model gas exhibited an A/F of 30 and had a temperature of 650° C. Then, the $NO_x$-sensing device according to the present example gave a corrected value "X," a corrected $NO_x$ concentration (or corrected detected-$NO_x$ concentration or value), of about 497 ppm. Thus, the outcomes of the evaluation test revealed that the $NO_x$-sensor correcting method and $NO_x$-sensing device according to the present example make it possible to approximate the raw or as-detected $NO_x$ concentrations (or detected $NO_x$ concentrations or values) to, or make them virtually equal to, the real or exact $NO_x$ concentrations (or true $NO_x$ concentrations or values).

Note that, in the $NO_x$-sensor correcting method and $NO_x$-sensing device according to the present example, the corrective map is made up of the temperature physical quantities that are divided into predetermined categories, the oxygen-concentration physical quantities that are divided into another predetermined categories, and the averaged values "Z" of the existing proportions of $NO_2$ or NO in the mixture of $NO_2$ and NO, existing proportions which come in the categories of the temperature physical quantities and oxygen-concentration physical quantities. Dividing the temperature physical quantities and oxygen-concentration physical quantities into much finer categories results in relating the existing proportions of $NO_2$ or NO in the mixture of $NO_2$ and NO to the temperature physical quantities and oxygen-concentration physical quantities much more precisely. Accordingly, it is possible to determine the averaged values "Z," the existing proportions of $NO_2$ or NO in the mixture of $NO_2$ and NO, with much higher accuracy. Consequently, it is possible to correct the raw or as-detected $NO_x$ concentrations (or detected $NO_x$ concentrations or values) much more precisely.

Moreover, the raw or as-detected $NO_x$ concentrations (or detected $NO_x$ concentrations or values) were corrected in compliance with claimed expression (1), that is, "X"="A"/(1+"B"×"Z"−"Z"), in the $NO_x$-sensor correcting method and $NO_x$-sensing device according to the specific example of the present invention. However, in the present invention, it is allowable to correct the raw or as-detected $NO_x$ concentrations (or detected $NO_x$ concentrations or values) by employing the other expressions like above-described equations (I) through (V) that are used to derive claimed expression (1).

In addition, in the $NO_x$-sensor that is applied to the $NO_x$-sensor correcting method and $NO_x$-sensing device according to the specific example of the present invention, the second diffusion-resistance layer 22 was used to divide the claimed exhaust-gas chamber into the first exhaust-gas chamber 31 and the second exhaust-gas chamber 32. However, in the present invention, the second diffusion-resistance layer 22 is not an indispensable constituent element at all. That is, it is permissible to dispose the inner oxygen-pumping electrode 61 and the inner oxygen-detecting electrode 63 as well as the inner $NO_x$-detecting electrode 65 in an independent or single exhaust-gas chamber when electrodes with good oxygen-pumping capability are used as the inner and outer oxygen-pumping electrodes 61 and 62, or when a plurality of oxygen-pumping electrodes are disposed in the one and only independent exhaust-gas chamber, for instance.

Having now fully described the present invention, it will be apparent to one of ordinary skill in the art that many changes and modifications can be made thereto without departing from the spirit or scope of the present invention as set forth herein including the appended claims.

What is claimed is:

1. A method of correcting $NO_x$ sensor, the method being adapted for correcting an $NO_x$ concentration that an $NO_x$ sensor detects actually, the $NO_x$ sensor being disposed in an exhaust-gas flow passage of vehicle, and comprising a porous diffusion-resistance layer, an exhaust-gas chamber into which exhaust gases that have passed through the porous diffusion-resistance layer are introduced, and a detective unit for detecting an $NO_x$ concentration in the exhaust gases that are introduced into the exhaust-gas chamber, the method comprising the steps of:
preparing a corrective map in advance, the corrective map recording relationships between temperature physical quantities that are relevant to a temperature of the exhaust gases, oxygen-concentration physical quantities that are relevant to an oxygen concentration in the exhaust gases, and an existing proportion of at least one of NO and $NO_2$ in a mixture of $NO_x$ in the exhaust gases before passing through the porous diffusion-resistance layer;

finding the existing proportion with reference to the corrective map using the temperature physical quantities that are detected actually and the oxygen-concentration physical quantities that are detected actually; and correcting the $NO_x$ concentration, which the $NO_x$ sensor detects actually, on the basis of not only the existing proportion but also a difference between an $NO_2$ diffusion velocity and an NO diffusion velocity.

2. The method according to claim 1, wherein:
the detective unit comprises:
an oxygen-pumping electrode for discharging oxygen in the exhaust gases, which are introduced into the exhaust-gas chamber, to the outside of the exhaust-gas chamber;
an oxygen-detecting electrode for outputting an oxygen-detection electric current whose magnitude corresponds to a first amount of oxygen that remains inside the exhaust-gas chamber; and
an $NO_x$-detecting electrode for outputting an $NO_x$-detection electric current whose magnitude corresponds to a sum of the first amount of oxygen and a second amount of oxygen that is contained in NO inside the exhaust-gas chamber;
the $NO_x$ sensor detects an $NO_x$ concentration inside the exhaust-gas chamber on the basis of a difference between the oxygen-detection electric current and the $NO_x$-detection electric current; and
the $NO_x$ concentration, which the $NO_x$ sensor detects actually, is corrected by following expression (1):

$$"X"="A"/(1+"B"\times"Z"-"Z") \qquad (1)$$

wherein "X" specifies a corrected $NO_x$ concentration;
"A" specifies an $NO_x$ concentration that the $NO_x$ sensor detects actually;
"B" specifies a value that is obtained by dividing an $NO_2$ diffusion velocity by an NO diffusion velocity; and
"Z" specifies a value that is obtained by dividing an $NO_2$ concentration in the exhaust gases before passing through the porous diffusion-resistance layer by a sum of the $NO_2$ concentration in the exhaust gases before passing through the porous diffusion-resistance layer and an NO concentration in the exhaust gases before passing through the porous diffusion-resistance layer.

3. The method according to claim 2, wherein the term "B" in expression (1) falls in a range of from 0.79 to 0.82.

4. The method according to claim 1, wherein the temperature physical quantities are made up of at least one member that is selected from the group consisting of actual temperatures of the exhaust gases, and temperatures of the exhaust gases that are computed indirectly from temperatures of exhaust system.

5. The method according to claim 1, wherein the oxygen-concentration physical quantities are made up of at least one member that is selected from the group consisting of actual oxygen concentrations in the exhaust gases, and oxygen concentrations in the exhaust gases that are computed indirectly from air-fuel ratios.

6. An $NO_x$-sensing device, comprising;
an $NO_x$ sensor being disposed in an exhaust-gas flow passage of vehicle, and comprising a porous diffusion-resistance layer, an exhaust-gas chamber into which exhaust gases that have passed through the porous diffusion-resistance layer are introduced, and a detective unit for detecting an $NO_x$ concentration in the exhaust gases that are introduced into the exhaust-gas chamber;
a corrective map recording relationships between temperature physical quantities that are relevant to a temperature of the exhaust gases, oxygen-concentration physical quantities that are relevant to an oxygen concentration in the exhaust gases, and an existing proportion of at least one of NO and $NO_2$ in a mixture of $NO_x$ in the exhaust gases before passing through the porous diffusion-resistance layer;

a first detector for detecting the temperature physical quantities;

a second detector for detecting the oxygen-concentration physical quantities; and a calculator for finding the existing proportion with reference to the corrective map using the temperature physical quantities that are detected actually and the oxygen-concentration physical quantities that are detected actually, and then correcting the $NO_x$ concentration, which the $NO_x$ sensor detects actually, on the basis of not only the existing proportion but also a difference between an $NO_2$ diffusion velocity and an NO diffusion velocity.

7. The $NO_x$-sensing device according to claim 6, wherein: the detective unit comprises:

an oxygen-pumping electrode for discharging oxygen in the exhaust gases, which are introduced into the exhaust-gas chamber, to the outside of the exhaust-gas chamber;

an oxygen-detecting electrode for outputting an oxygen-detection electric current whose magnitude corresponds to a first amount of oxygen that remains inside the exhaust-gas chamber; and an $NO_x$-detecting electrode for outputting an $NO_x$-detection electric current whose magnitude corresponds to a sum of the first amount of oxygen and a second amount of oxygen that is contained in NO inside the exhaust-gas chamber;

the $NO_x$ sensor detects an $NO_x$ concentration inside the exhaust-gas chamber on the basis of a difference between the oxygen-detection electric current and the $NO_x$-detection electric current; and the calculator corrects the $NO_x$ concentration, which the $NO_x$ sensor detects actually, by following expression (1):

$$\text{``}X\text{''} = \text{``}A\text{''}/(1 + \text{``}B\text{''} \times \text{``}Z\text{''} - \text{``}Z\text{''}) \tag{1}$$

wherein "X" specifies a corrected $NO_x$ concentration;

"A" specifies an $NO_x$ concentration that the $NO_x$ sensor detects actually;

"B" specifies a value that is obtained by dividing an $NO_2$ diffusion velocity by an NO diffusion velocity; and "Z" specifies a value that is obtained by dividing an $NO_2$ concentration in the exhaust gases before passing through the porous diffusion-resistance layer by a sum of the $NO_2$ concentration in the exhaust gases before passing through the porous diffusion-resistance layer and an NO concentration in the exhaust gases before passing through the porous diffusion-resistance layer.

8. The $NO_x$-sensing device according to claim 7, wherein the term "B" in expression (1) falls in a range of from 0.79 to 0.82.

9. The $NO_x$-sensing device according to claim 6, wherein the temperature physical quantities are made up of at least one member that is selected from the group consisting of actual temperatures of the exhaust gases, and temperatures of the exhaust gases that are computed indirectly from temperatures of exhaust system.

10. The $NO_x$-sensing device according to claim 6, wherein the oxygen-concentration physical quantities are made up of at least one member that is selected from the group consisting of actual oxygen concentrations in the exhaust gases, and oxygen concentrations in the exhaust gases that are computed indirectly from air-fuel ratios.

11. The $NO_x$-sensing device according to claim 6, wherein a thermometer comprising a thermo couple makes the first detector.

12. The $NO_x$-sensing device according to claim 6, wherein the second detector comprises paired oxygen-pumping electrodes, paired oxygen-detecting electrodes, and paired $NO_x$-detecting electrodes.

* * * * *